United States Patent
Palpu et al.

(10) Patent No.: US 7,344,739 B2
(45) Date of Patent: Mar. 18, 2008

(54) ANTI-ALLERGIC HERBAL FORMULATION

(75) Inventors: Pushpangadan Palpu, Lucknow (IN); Chandana Venkateswara Rao, Lucknow (IN); Ajay Kumar Singh Rawat, Lucknow (IN); Sanjeev Kumar Ojha, Lucknow (IN); Gaddam Dayanand Reddy, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 11/024,021

(22) Filed: Dec. 28, 2004

(65) Prior Publication Data

US 2006/0141067 A1    Jun. 29, 2006

(51) Int. Cl.
*A01N 65/10* (2006.01)
(52) U.S. Cl. ........................................ 424/734
(58) Field of Classification Search ............... None
See application file for complete search history.

(56) References Cited

U.S. PATENT DOCUMENTS 6,235,287 B1 * 5/2001 Weidner et al. ............. 424/756

OTHER PUBLICATIONS

Tripathi et al, Effect of Histamine & Albizzia lebbek Benth. on Guineapig Adrenal Glands, Indian Journal of Experimental Biology, vol. 17, Sep. 1979, pates 915-917.*

S. S. Gupta, Prospects and Perspectives of Natural Plants Products In Medicine, Indian Journal of Phamacology, 1994; vol. 26, pp. 1-12.*

Mujumdar et al, Antiinflammatory activity of Curcuma Amada RoxB. In Albino Rats, Indian Journal of Pharmacology, 2000, vol. 32, pp. 375-377.*

S. S. Singh, Chemistry and Medicinal Properties of Tinospora Cordifolia (Guduchi), Indian Journal of Pharmacology, 2003, vol. 35, pp. 83-91.*

Amit et al, Safety of a Novel Botanical Extract Formula for Ameliorating Allergic Rhinitiis, Toxicology Mechanisms and Methods, 2003, vol. 13, pp. 253-261.*

* cited by examiner

*Primary Examiner*—Christopher R. Tate
*Assistant Examiner*—Deborah A. Davis
(74) *Attorney, Agent, or Firm*—Ladas and Parry LLP

(57) ABSTRACT

The invention provides a novel herbal preparation useful in treatment of allergy. Formulation(s) comprises of plant preparation or active component of plant extract together with conventional additives to form the oral dosage forms, which includes tablets, capsules and liquid dosage forms viz. syrup and suspension as anti-allergic. Formulation(s) comprises of *Tinospora cardifolia, Piper longum, Albizia lebbeck* and *Curcuma amada*. The formulation can be used as solid or liquid or encapsulated as a soft/hard gelatin capsule for easy consumption as solid or liquid dosage forms.

8 Claims, No Drawings

ANTI-ALLERGIC HERBAL FORMULATION

FIELD OF THE INVENTION

The present invention relates to novel herbal formulation(s) useful as anti-allergens.

BACKGROUND AND PRIOR ART OF THE INVENTION

Stress is known to alter the physiological homeostasis of the organism and results in the break down of the integrated adaptational processes. In response to extreme environmental demands various endocrinal and visceral responses occur naturally in a variety of experimental situations. For example, changes in plasma corticosterone and gastric mucosal integrity are widely reported during stress and both peripheral and central mechanisms seemingly regulate these changes. Much interest has recently been generated on the immunological changes during stress with reports indicating that the immune status of the organism is actually modified by experimental stressors. The central nervous system, besides being crucial for stress, also regulates immune function and studies show that common neural substrates like the hypothalamus are clearly involved in such central nervous system-immune system interactions.

Neuro-pharmacological data have shown that complex neurochemical mechanisms regulates stress responses and transmitters like gamma-aminobutyric acid (GABA) and endogenous opiates are crucially involved. For example, benzodiazepenes (BZD), which modulate GABA, and opioid antagonists, modify several stress responses like gastric ulcer formation and plasma corticosterone. Evidence indicates that central nervous system innervation of lymphoid tissue is possible. Lymphocytes bear receptors for several hormones and neurotransmitters and pharmacological alterations in neural activity influence immunocompetence. (Ray 1991)

Scientists now use the word anaphylaxis to mean any immune reaction of this type, even if it is not serious. But most doctors use it to mean life-threatening rapid allergic reaction. Unfortunately this kind of harmful immunization happens to a few of us not just from injections but also from ordinary foods such as nuts. Our immune system is there to protect us from infection, goes wrong and harms or even kills us. In recent years, there has been an upsurge in the clinical use of indigenous drugs. Such herbal plants, originally used in the traditional system of medicine, are now being effectively tried in a variety of path physiological states. Non-specific mechanisms like restoration of normal physiological milieu and generalized increase in resistance against infections are proposed and the role of the immune system in these drug effects is suggested. (Sen P et al., 1992).

OBJECT OF THE INVENTION

The main object of the present invention is to provide a novel Anti-allergic herbal formulation(s) in various dosage forms viz; tablet, capsule and ointment form for easy consumption.

Another objective of the present invention is to prepare herbal dosage form that improves in the treatment of allergy.

SUMMARY OF THE INVENTION

Accordingly, the present invention provides a novel of the invention of an herbal formulation(s) obtained from plants having the property of stimulant and resistant to various pathogens and acts as an immunomodulation as a tablet, injection and as a liquid formulation(s).

The herbal synergistic formulation has anti-allergy properties and comprises extracts of *Tinospora cardifolia*, *Piper longum*, *Albizia lebbeck* and *Curcunia amada*.

In an embodiment the extracts/juice of the plants are mixed in the ratio viz *Tinospora cardifolia* (2-3 wt %), *Piper longum* (0.5-2 wt %), *Albizzia lebbeck* (3-5 wt %), and *Curcuma amada* (3-5 wt %) and balance being conventional additives.

In another embodiment, the plant used is *Tinospora cardifolia*.

In another embodiment, the plant used is *Piper longum*.

In another embodiment, the plant used is *Albizia lebbeck*.

In still another embodiment, the plant used is *Curcuma amada*.

In another embodiment, composition is used a syrup or suspension.

In another embodiment, the formulation is also used as anti-oxidant and nerves relaxant.

In still another embodiment, the formulation is also used to treat allergic related diseases, blood purifier, anti-periodic and externally applied sprain and wound.

In another embodiment, the formulation is also used as a blood purifier and for jaundice treatment.

In yet another embodiment, the said formulation has specific gravity ranging between 0.972-1.405 and a refractive index ranging between 1.5263-1.6812.

In another embodiment, the formulation at a dose of 400 mg/kg did not show any abnormality of general condition.

In another embodiment, the formulation form at a dose ranging from 100-200 mg/kg shown a 22.70-80.04% protection in hypoxia time and works as a stress relaxant.

In another embodiment, the formulation form at a dose ranging from 100-200 mg/kg shown a 24.18-82.83% protection in swimming endurance and works as a stress relaxant.

DETAILED DESCRIPTION OF THE INVENTION

Accordingly the present invention provides a novel Anti-allergic herbal formulation(s) in various dosage forms viz; tablet, capsule and ointment form for easy consumption. The herbal formulation comprising of *Tinospora cardifolia*, *Piper longum*, *Albizia lebbeck* and *Curcuma amada*. *Tinospora cardifolia* extract brown in color. It is used as nourishing food. It was shown that it produce a significant improvement in general ability and behavioural pattern.

*Tinospora cordifolia* Family. Menisperniaceae
Botanical Descriptions: A large glabrous climbing shrub. Stems rather succulent with long filiform, aerial roots arising from branches. Bark; warty, papery thin, creamy white or grey brown. Peels off easily. Wood, soft, perforated. Leaves; membranous, cordate with broad sinus. Pointed at the tip. Flowers; unisexual and greenish, in long clusters. Seeds; curved. Drupes; ovoid, succulent, lustrous, red, pea sized. Fruits; fleshy, one seeded. It is found throughout tropical India, ascending to an altitude of 300 m.
Medicinal Uses: Useful in bilious fever, rheumatism, general debility, seminal weakness, splenic diseases and urinary affections. Fresh plant is considered more efficacious. It is mostly used for preparing a kind of starch known as *Guduchi satva* or *Sat giloe*.

Phytochemistry: Sesquiterpene tinocordifolin, sesquiterpene glucoside tinocordifolioside, tinosponone, tinocordioside, cordioside, furanoid diterpenes, a new clerodane furanoditerpene viz. columbin, tinosporaside, an immunologically active arabinogalactan, two phytoecdyyones viz., ecdysterone and makisterone and several glycosides isolated as polyacetates. Other alkaloids viz., jatrorrhizine, palmatine, berberine, tembeterine, phenylpropene disaccharides cordifolioside A, B and C, choline, tinosporic acid, tinosporal, tinosporon, 20-β-hydroxyecdysone, palmatoside C and F, cordifolisides D and E, diterpenoid furanolactones.

Pharmacology: The water and ethanolic extract inhibited the cyclophosphamide induced immunosupression. Aqueous extract of the stem showed anti-inflammatory, analgestic and antipyretic properties in rats. In clinical studies, it also showed immunosuppressive effect in obstructive jaundice patients, antioxidant activity and amelioration of cylcophosphamide-induced toxicity.

*Piper longum* L. Family: Piperaceae

Botanical Description: A slender, aromatic climber with perennial woody roots; stems jointed, creeping, young shoots downy. Leaves simple, alternate, 5-12 cm long and 3-6 cm wide, glabrous, ovate base cord ate with broad rounded lobes, apex sub acute, and margins entire. Flowers minute on unisexual, axillary, cylindrical spikes; green at first, turning yellow, up to 5 cm long; male spikes longer than female. Fruits ovoid, yellowish orange turning dark red to blackish, sunk in fleshy spikes 2.5-3.8 cm long.

Pharmacology: The dried roots, as well as the immature and mature fruits, are used extensively, alone and in combination with other plant drug to treat a broad range of ailments in traditional Indian medicine. The dried roots and thicker stems, known commercially as piplamul, are an important drug in the ayurvedic and unani systems. The roots and fruits are used to treat dysentery and leucoderma, as a cholagogue for treating bileduct and gallbladder obstruction, and as a counter—irritant and analgesic for relieving muscularpains and inflammations. A decoction of dried immature fruit and root, or the powdered fruits mixed with honey, is used to treat chronic bronchitis, cough and cold. An infusion of the powdered fruits is given to women after childbirth to check bleeding and fever. It is as important ingredient in medicated oil used externally for sciatica and paraplegia.

*Albizia lebbeck* Family: Mimosoideae

Botanical description: It is common throughout India, from the plains up to 900 m elevations in the Himalayas. It is a large, unarmed, decidous tree to about 20 m tall with a spreading crown; bark pale; young shoots glabrous. Leaves bipinnate; rachis with a gland near the base of the petiole and one below uppermost pairs of pinnae; pinnae usually 2-3 pairs, 7-12 cm long; leaflets 5-9 pairs, 2.5-4.5 cm long and 1.6-2 cm wide, with glands between their bases, elliptic-oblong or obovate-oblong, unequal-sided, retuse or obtuse at apex, base obliquely rounded or truncate; petiolules very short. Flowers fragrant, white to greenish-yellow, borne in globose umbellate heads 2-3.8 cm in diameter; peduncles 3.8-7.5 cm long, solitary or 2-4 together from the axils of the upper leaves, pedicels 2.5-3 mm long; calyx 4 mm long, pubescent, teeth short, deltoid; corolla 1 cm long, tube glabrous, lobes 2.5 mm long, triangular, acute, pubescent outside; stamens longer than the corolla. Fruits (pods) 10-30 cm long and 2-4.5 cm wide, linear-oblong, bluntly pointed, thin green turning straw-coloured on maturity, reticulately veined above the seeds, smooth, shining; seeds 4-12, pale brown, ellipsoid-oblong, compressed. Flowers from April to June and fruits mature in December in northern and central India; in southern India flowering occurs earlier, from January to April. In central India trees remains leafless for a month or more between March and June.

Medicinal uses: In Ayurveda the astringent root is used to treat hemicrania; the acrid bark is reportedly used to treat diseases of the blood, leucoderma, itching, skin diseases, piles, inflammation, and bronchitis; the leaves are used to treat opthalmia, and the flowers for asthma. In unani medicine the root is used to treat ophthalmia; the bark is regarded as anthelmintic and used to relieve toothache and to strengthens the gums and teeth, and to treat leprosy, deafness, boils, scabies, syphilis and paralysis; the leaves are reportedly useful for treating night blindness; and the seeds are used to treat gonorrhoea and tuberculous glands, their oil applied locally for leucoderma. The flower are used as a cooling medicine and as an external application to relieve boils, skin eruption and swelling the seed oil is used externally to promote healing of lesions in leprosy among the Irulars of Tamilnadu.

Phytochemistry: A new acyclic ester isolated and characterized as heneicos-7 (2)-enyl-24-hydroxytetracos-10 (2)-enoate; lupeol, oleanolic acid, docosanoic acid and β-sitosterol also was isolated (*Ind J Pharm Sci,* 1991,53,24). Echinocystic acid β-sitosterol identified in bark and seeds (*Ind J Appl. Chem,* 1969,32,73; *Chem Abstr* 1971,75, 160352). Mature leaves contained ketoacids including phosphoenol pyruvate, glyoxalate, oxaloacetate and α-oxoglutarate (*Plant Biochem J,* 1977,4,34; Chem Abstr 1977,17,148762s); vicenin-2, reynoutrin, rutin, myricitrin and robinin from leaves (*Shoyakugaku Zasshi;* 1977, 31, 172; *Chem Abstr* 1978,88,14897h).

Pharmacology: Bark and flowers decoction protected guinea pig against histamine and acetlycholine-induced bronchospam. Chronic treatment with bark decoction also protected sensitized guinea pigs against antigen challenge. Drug showed anti-asthmatic and anti-anaphylactic activities due to inhibition of phenomenon of sensitization (*Ind J Pharmacol,* 1977,9,189). Saponin showed β-haemolysis against buffalo and sheep blood and α-haemolysis against human blood. Purified saponin showed antifungal activity against marcophomnina phaseolina (mic 32.8 μg), stemphilum species and *fusarium* solani (*Pak Vet J* 1990,10, 146; *Chemi Abstr* 1992,116,102686j). The plant has been showed to poses antidirrhoeal and antifertility activities. It posses anti anaphylactic and anticonvulsive properties. The leaves are reportedly useful for treating night blindness; and the seeds are used to treat gonorrhoea and tuberculous glands, their oil applied locally for leucoderma.

*Curcuma amada* Family: Zingiberaceae

Botanical description: A tall herb, rootstock large, ovoid, with cylindrical tubers that are bright yellow or orange inside. Leaves very large, in tufts up to 1.2 m long including petioles, blade up to 50 cm long and 8 cm wide, oblong lanceolate, tapering to the base; petiole about as long as leaf blade. Flowers are pale yellow.

Pharmacology: The dried, powdered rhizome is the source of turmeric, widely used in Indian cuisine as well as in traditional medicine. Turmeric is considered to have strong antiseptic properties and is used to treat poisonous affections, ulcers and wounds. In Ayurveda, is considered to be alterative, antiperiodic, germicidal, carminative, stimulant, tonic and vermifuge. It is used to treat diabetes, eye diseases, ulcers, oedema, anaemia, anorexia, leprosy, scrofula; its paste, sometimes combined with that of neem leaves, is used to cure ring worm, itching, eczema and other parasitic skin diseases, and in the treatment of chicken pox and small pox. In unani medicine it is considered carminative, mutant and diuretic and useful for treating jaundice and other liver disorders. An essential oil obtained from the rhizome is used as a carminative, stoma chic and tonic. A paste made of the flowers is used externally to treat ringworm and other parasitic skin diseases, as well as gonorrhoea.

Medicinal uses: It is used to treat diabetes, eye diseases, ulcers, oedema, anaemia, anorexia, leprosy, scrofula; its paste, sometimes combined with that of neem leaves, is used to cure ring worm, itching, eczema and other parasitic skin diseases, and in the treatment of chicken pox and small pox.

The present invention provides a novel of the invention of an herbal formulation(s) obtained from plants having the property of stimulant and resistant to various pathogens and acts as an immunomodulation as a tablet, injection and as a liquid formulation(s).

The herbal synergistic formulation has anti-allergy properties and comprises extracts of *Tinospora cardifolia*, *Piper longum*, *Albizia lebbeck* and *Curcuma amada*. The extracts/juice of the plants are mixed in the ratio viz *Tinospora cardifolia* (2-3 wt %), *Piper longum* (0.5-2 wt %), *Albizzia lebbeck* (3-5 wt %), and *Curcuma amada* (3-5 wt %) and balance being conventional additives.

In another embodiment, the plant used is *Tinospora cardifolia*.

In another embodiment, the plant used is *Piper longum*.

In another embodiment, the plant used is *Albizia lebbeck*.

In still another embodiment, the plant used is *Curcuma amada*.

In another embodiment, composition is used a syrup or suspension.

The formulation is also used as anti-oxidant and nerves relaxant. The formulation can also be used to treat allergic related diseases, blood purifier, anti-periodic and externally applied sprain and wound. The formulation is also used as a blood purifier and for jaundice treatment.

The formulation has specific gravity ranging between 0.972-1.405 and a refractive index ranging between 1.5263-1.6812. At a dose of 400 mg/kg did not show any abnormality of general condition. The formulation form at a dose ranging from 100-200 mg/kg shown a 22.70-80.04% protection in hypoxia time and works as a stress relaxant.

The formulation form at a dose ranging from 100-200 mg/kg shows 24.18-82.83% protection in swimming endurance and works as a stress relaxant.

The invention is further illustrated by the following non-limiting examples.

Formulation 1 (F1)

| *Tinospora cardifolia* | 3 wt. % |
|---|---|
| Lactose | 66.7 g |
| Starch | 10 g |
| Water | q.s. to make 100 ml |

Dry mature seed of *Tinospora cardifolia* are washed in purified distilled water, and were immersed in hot water (30-60° C.) for 2-3 hr. Mix the plant constituents and filter the solution and add specified quantity of starch and heat until the starch dissolves and then cool and make up the volume with required amount of water to make 100 ml. Oral dosage form has been described in detail giving the formula of the ingredients along with the method and mode of usage of the standardized formulation. Kindly refer table I and II.

Formulation 2 (F2)

| *Piper longum* | 1 wt. % |
|---|---|
| Lactose | 66.7 g |
| Starch | 10.0 g |
| Water | q.s. to make 100 ml |

Dry mature seed of *Piper lonigum* are washed in purified distilled water, and were immersed in hot water (30-60° C.) for 2-3 hr. Mix the plant constituents and filter the solution and add specified quantity of starch and heat until the starch dissolves and then cool and make up the volume with required amount of water to make 100 ml. Oral dosage form has been described in detail giving the formula of the ingredients along with the method and mode of usage of the standardized formulation. Kindly refer table I and II.

Formulation 3 (F3)

| *Albizia lebbeck* | 4 wt. % |
|---|---|
| Lactose | 66.7 g |
| Starch | 10.0 g |
| Water | q.s. to make 100 ml |

Dry mature seed of *Albizia lebbeck* are washed in purified distilled water, and were immersed in hot water (30-60° C.) for 2-3 hr. Mix the plant constituents and filter the solution and add specified quantity of starch and heat until the starch dissolves and then cool and make up the volume with required amount of water to make 100 ml. Oral dosage form has been described in detail giving the formula of the ingredients along with the method and mode of usage of the standardized formulation. Kindly refer table I and II.

Formulation 4 (F4)

| *Curcuma amada* | 5 wt % |
|---|---|
| Lactose | 66.7 g |
| Starch | 10 g |
| Water | q.s. to make 100 ml |

Dry mature seed of *Curcuma amada* are washed in purified distilled water, and were immersed in hot water (30-60° C.) for 2-3 hr. Mix the plant constituents and filter the solution and add specified quantity of starch and heat until the starch dissolves and then cool and make up the volume with required amount of water to make 100 ml. Oral dosage form has been described in detail giving the formula of the ingredients along with the method and mode of usage of the standardized formulation (Tables I and II)

Formulation 5 (F5)

| *Tinospora cardifolia* | 3 wt. % |
|---|---|
| *Piper longum* | 1 wt. % |
| Lactose | 63.7 g |
| Starch | 10 g |
| Water | q.s. to make 100 ml |

Dry mature seed of *Tinospora cardifolia* and *Piper longum* are washed in purified distilled water, and immersed in hot water (30-60° C.) for 2-3 hr. Mix the plant constituents and filter the solution and add specified quantity of starch and heat until the starch dissolves and then cool and make up the volume with required amount of water to make 100 ml. Oral dosage form has been described in detail giving the formula of the ingredients along with the method and mode of usage of the standardized formulation (Tables I and II).

Formulation 6 (F6)

| | | |
|---|---|---|
| *Tinospora cardifolia* | 3 wt. % | |
| *Piper longum* | 1 wt. % | |
| *Albizia lebbeck* | 3 wt. % | |
| Lactose | 60.7 g | |
| Starch | 10 g | |
| Water | q.s. to make 100 ml | |

Dry mature seed of *Tinospora cardifolia*, *Piper longum* and *Albizia lebbeck* are washed in purified distilled water, and immersed in hot water (30-60° C.) for 2-3 hr. The plant constituents were mixed and the solution filtered and specified quantity of starch added and heated till starch dissolves and then cooled and volume made up with required amount of water to make 100 ml. Oral dosage form has been described in detail giving the formula of the ingredients along with the method and mode of usage of the standardized formulation. Kindly refer table I and II.

Formulation 7(F7)

| | | |
|---|---|---|
| *Tinospora cardifolia* | 3 wt. % | |
| *Piper longum* | 1 wt. % | |
| *Albizia lebbeck* | 4 wt. % | |
| *Curcuma amada* | 3 wt. % | |
| Lactose | 56.7 g | |
| Starch | 10 g | |
| Water | q.s. to make 100 ml | |

Dry mature seed of *Tinospora cardifolia*, *Piper longum*, *Albizia lebbeck* and *Curcuma amada* are washed in purified distilled water, and were immersed in hot water (30-60° C.) for 2-3 hr. Mix the plant constituents and filter the solution and add specified quantity of starch and heat until the starch dissolves and then cool and make up the volume with required amount of water to make 100 ml. Oral dosage form has been described in detail giving the formula of the ingredients along with the method and mode of usage of the standardized formulation. Kindly refer table I and II.

TABLE I

Effect of formulation on hypoxia and swimming performance time in mice.

| S. No | Treatment | Dose (mg/kg, p.o) | Hypoxia time | Swimming endurance |
|---|---|---|---|---|
| 1. | Control + Stress | — | 23.34 ± 1.15 | 238.21 ± 25.11 |
| 2. | F1 | 200 | 24.34 ± 1.55 | 241.21 ± 27.41 |
| 3. | F2 | 200 | 22.54 ± 2.11 | 239.45 ± 25.05 |
| 4. | F3 | 200 | 26.01 ± 2.28 | 245.52 ± 26.74 |
| 5. | F4 | 200 | 27.89 ± 2.15 | 246.32 ± 25.53 |
| 6. | F5 | 200 | 27.01 ± 2.58 | 248.14 ± 26.85 |
| 7. | F6 | 200 | 35.23 ± 2.95[a] | 369.52 ± 26.74[a] |
| 8. | F7 | 200 | 45.89 ± 3.05[b] | 435.54 ± 28.85[b] |

Values are mean ± S.E.M.
P: [a]<0.01 and [b]<0.001 compared to control + stress group.
NOTE:
No mortality was found in any of the treated group.

No gross abnormality in behavior was observed in the animal exposed with herbal preparation. The formulation (F1) contains *Tinospora cardifolia* (3%) with balance being conventional additives. The formulation (F2) contains *Piper longum* (1%) with balance being conventional additives. The formulation (F3) contains *Albizia lebbeck*. (4%) with balance being conventional additives. The formulation (F4) contains *Curcuma amada* (3%) with balance being conventional additives. The formulation (F5) contains *Tinospora cardifolia* (3%) and *Piper longum* (1%) with balance being conventional additives. The formulation (F6) contains *Tinospora cardifolia* (3%), *Piper longum* (1%) and *Albizia lebbeck* (3%) with balance being conventional additives. The formulation (F7) contains *Tinospora cardifolia* (3%), *Piper longum* (1%), *Albizia lebbeck* (4%) and *Curcuma amada* (3%) with balance being conventional additives The results showed in table 1 that formulations F7 showed significant hypoxia time when compared with control+stress and formulation F1-F6. The value of formulation F7 hypoxia time has significantly increased and swimming endurance value is decreased which leads to stress relaxation.

Immunological Assay

Hypoxia time: The animals were placed in an empty glass jar of 300 mL capacity attached with an electronic watch; the jars were made air tight with greased glass stoppers and the time until the onset of convulsion was recorded (Singh B et al 2001).

Swimming performance time: The animals were allowed to swim inside a Perspex glass beaker (30 cm high with 20 cm diameter containing water up to 25 cm high) maintained at 26°±1° C. with a continuous air current from the bottom. The end point of swimming endurance was taken as when the mice remained at the bottom for more than 10 s (Singh B et al 2001).

TABLE II

Effect of formulation on mast cell degranulation in rats.

| S. No | Treatment | Dose (mg/kg, p.o) | Histamine released (µg/ml) |
|---|---|---|---|
| 1. | Control | — | 0.899 ± 0.05 |
| 2. | F1 | 200 | 0.895 ± 0.04 |
| 3. | F2 | 200 | 0.886 ± 0.06 |
| 4. | F3 | 200 | 0.892 ± 0.05 |
| 5. | F4 | 200 | 0.879 ± 0.05 |
| 6. | F5 | 200 | 0.885 ± 0.02 |
| 7. | F6 | 200 | 0.671 ± 0.02[a] |
| 8. | F7 | 200 | 0.254 ± 0.05[c] |
| 9. | Avil | 25 | 0.345 ± 0.04[b] |

Values are mean ± S.E.M.
P: [a]<0.05, [b]<0.01 and [c]<0.001 compared to control group.
NOTE:
No mortality was found in any of the treated group.

No gross abnormality in behavior was observed in the animal exposed with herbal preparation.

The formulation (F1) contains *Tinospora cardifolia* (3%) with balance being conventional additives. The formulation (F2) contains *Piper longum* (1%) with balance being conventional additives. The formulation (F3) contains *Albizia lebbeck.* (4%) with balance being conventional additives. The formulation (F4) contains *Curcuma amada* (3%) with balance being conventional additives. The formulation (F5) contains *Tinospora cardifolia* (3%) and *Piper longum* (1%) with balance being conventional additives. The formulation (F6) contains *Tinospora cardifolia* (3%), *Piper longum* (1%) and *Albizia lebbeck* (3%) with balance being conventional additives. The formulation (F7) contains *Tinospora cardifolia* (3%), *Piper longum* (1%), *Albizia lebbeck* (4%) and *Curcuma amada* (3%) with balance being conventional additives.

The results showed in table 2 formulations F7 showed significant effect when compared with control. The release of histamine is tremendously decreased which shows the anti allergic activity. The formulation F7 is more significant than that of standard drug Avil.

Disadvantages of Avil are Dizziness and Drowsiness.

Mast cell degranulation: Tyrode solution (10 ml) containing 5 units/ml of heparin was injected in the peritoneal cavity of sensitized male rats lightly anaesthetized with ether. After a gentle abdominal massage for about 30 to 45 sec, the mast cell rich peritoneal fluid was collected over ice and centrifuged at 2000 rpm for 5 min. The cells were washed thrice with chilled Tyrode and resuspended in about 1 ml of Tyrode solution. The peritoneal fluid was obtained from 10 rats and the final volume of the fluid was pooled and used for the studies (Nair A M et al, 1997).

TABLE III

Effect of formulation (F7) on lipid peroxidation, superoxide dismutase and catalase activities in tissues.

| S. No | Treatment | Liver | Kidney | Heart |
|---|---|---|---|---|
| | | Lipidperoxidation(LPO) | | |
| 1. | Control | 32.2 ± 1.5 | 25.1 ± 1.3 | 17.7 ± 0.5 |
| 2. | F7 | 18.5 ± 1.2$^c$ | 13.65 ± 2.7$^c$ | 21.5 ± 2.1$^a$ |
| | | Superoxide dismutase(SOD) | | |
| 1. | Control | 9.2 ± 0.6 | 5.8 ± 0.9 | 4.3 ± 0.5 |
| 2. | F7 | 2.6 ± 0.8$^c$ | 3.6 ± 0.2$^b$ | 4.9 ± 0.4$^a$ |
| | | Catalase activity | | |
| 1. | Control | 96.3 ± 1.8 | 126.5 ± 1.9 | 92.5 ± 2.5 |
| 2. | F7 | 185.6 ± 7.1$^c$ | 256.9 ± 8.3$^c$ | 132.2 ± 3.4$^c$ |

Values are mean ± S.E.M.
P: $^a$<0.05, $^b$<0.01 and $^c$<0.001 compared to respective control group.
NOTE:
No mortality was found in any of the treated group.

No gross abnormality in behavior was observed in the animal exposed with herbal preparation.

The formulation (F7) contains *Tinospora cardifolia* (3%), *Piper longum* (1%), *Albizia lebbeck* (4%) and *Curcuma amada* (3%) with balance being conventional additives.

TABLE IV

Effect of formulation(s) on relative mean ± SEM organ weights of rats.

| Treatment group | Body weight (g) | Kidney (g) | Liver (g) | Spleen (g) |
|---|---|---|---|---|
| Control | 182.5 ± 9.3 | 0.94 ± 0.04 | 5.92 ± 0.65 | 0.61 ± 0.07 |
| F (5) | 171.3 ± 8.6 | 0.87 ± 0.05 | 5.68 ± 0.58 | 0.68 ± 0.05 |
| F (6) | 178.1 ± 9.7 | 0.92 ± 0.07 | 5.82 ± 0.61 | 0.70 ± 0.08 |
| F (7) | 185.4 ± 8.4 | 0.85 ± 0.09 | 5.13 ± 0.69 | 0.65 ± 0.06 |

The formulation (F5) contains *Tinospora cardifolia* (3%) and *Piper longum* (1%) with balance being conventional additives. The formulation (F6) contains *Tinospora cardifolia* (3%), *Piper longum* (1%) and *Albizia lebbeck* (3%) with balance being conventional additives. The formulation (F7) contains *Tinospora cardifolia* (3%), *Piper longum* (1%), *Albizia lebbeck* (4%) and *Curcuma amada* (3%) with balance being conventional additives.

The results of the Table IV shows there is no significant changes in body weight of various vital organs in the body in toxicity studies.

The formulation F5, F6 and F7 is highly effective (Table I) and it is safe.

Note: No mortality/gross abnormality was observed in the animals during the treatment of formulations (F5, F6 and F7).

We claim:

1. A herbal anti-allergy formulation comprising a mixture of juice or extract of
   (a) *Tinospora cordifolia* (2-3 wt %),
   (b) *Piper longum* (0.5-2 wt %),
   (c) *Albizzia lebbeck* (3-5 wt %),
   (d) *Curcuma amada* (3-5 wt %), and
   (e) balance comprising one or more pharmaceutically acceptable additives.

2. The herbal formulation as claimed in claim 1, wherein the formulation is a syrup or suspension.

3. The herbal formulation as claimed in claim 1, wherein the formulation has a specific gravity ranging between 0.972-1.405.

4. The herbal formulation as claimed in claim 1, wherein the formulation has a refractive index ranging between 1.5263-1.6812.

5. A method for the treatment of allergy in a subject comprising administering to the subject the herbal anti-allergy formulation according to claim 1.

6. A method as claimed in claim 5, wherein the formulation is used at a dose of 400 mg/kg body weight.

7. A method as claimed in claim 5, wherein the dosage is in the range of 100-200 mg/kg body weight and shows a 22.70-80.04% protection in hypoxia time and worked as a stress relaxant.

8. A method as claimed in claim 5, wherein the formulation at a dose ranging from 100-200 mg/kg body weight shows a 24.18-82.83% protection in swimming endurance and worked as a stress relaxant.

* * * * *